US009431694B2

(12) United States Patent
Li et al.

(10) Patent No.: US 9,431,694 B2
(45) Date of Patent: Aug. 30, 2016

(54) SYSTEMS AND METHODS FOR A DUAL BAND ANTENNA FOR AN INTERNAL MEDICAL DEVICE

(71) Applicant: PACESETTER, INC., Sylmar, CA (US)

(72) Inventors: Perry Li, Temple City, CA (US); Brett Villavicencio, Valencia, CA (US)

(73) Assignee: PACESESTTER, INC., Sylmar, CA (US)

(*) Notice: Subject to any disclaimer, the term of this patent is extended or adjusted under 35 U.S.C. 154(b) by 29 days.

(21) Appl. No.: 14/197,859

(22) Filed: Mar. 5, 2014

(65) Prior Publication Data
US 2015/0255858 A1  Sep. 10, 2015

(51) Int. Cl.
| H01Q 1/27 | (2006.01) |
|---|---|
| A61N 1/372 | (2006.01) |
| A61N 5/04 | (2006.01) |
| H01Q 5/371 | (2015.01) |

(52) U.S. Cl.
CPC .......... *H01Q 1/273* (2013.01); *A61N 1/37229* (2013.01); *A61N 5/04* (2013.01); *H01Q 5/371* (2015.01)

(58) Field of Classification Search
CPC ........ H01Q 1/273; H01Q 5/30; H01Q 5/307; H01Q 5/314; H01Q 5/321; H01Q 5/328; H01Q 5/378–5/392
USPC ...................................... 607/36, 60
See application file for complete search history.

(56) References Cited

U.S. PATENT DOCUMENTS

| 7,012,570 | B2* | 3/2006 | Chen ...................... H01Q 1/243 343/700 MS |
|---|---|---|---|
| 7,613,522 | B2 | 11/2009 | Christman et al. |
| 7,627,296 | B2 | 12/2009 | Kezys et al. |
| 8,285,387 | B2* | 10/2012 | Utsi ........................ H01Q 1/273 607/60 |
| 8,369,961 | B2 | 2/2013 | Christman et al. |
| 8,565,891 | B2* | 10/2013 | Mumbru ............ A61N 1/37229 607/32 |
| 2006/0084395 | A1 | 4/2006 | Kezys et al. |
| 2007/0288066 | A1 | 12/2007 | Christman et al. |
| 2009/0182388 | A1 | 7/2009 | Von Arx et al. |
| 2009/0182426 | A1 | 7/2009 | Von Arx et al. |
| 2009/0228076 | A1 | 9/2009 | Ameri |
| 2010/0016925 | A1 | 1/2010 | Christman et al. |
| 2011/0040159 | A1 | 2/2011 | Von Arx et al. |
| 2011/0082523 | A1* | 4/2011 | Nghiem ............ A61N 1/37229 607/60 |
| 2012/0142282 | A1 | 6/2012 | Kezys et al. |
| 2013/0012143 | A1 | 1/2013 | Kezys et al. |
| 2015/0130676 | A1* | 5/2015 | Chou ..................... H01Q 21/30 343/745 |

OTHER PUBLICATIONS

AT&T, Antenna Fundamentals Technical Brief, Dec. 2, 2009.*

* cited by examiner

Primary Examiner — Howard Williams

(57) ABSTRACT

A dual band antenna mounted to a case of an implantable medical device (IMD) for implant within a patient is provided. The dual band antenna includes a first antenna sub-structure (FAS) and a second antenna sub-structure (SAS) each separately tuned to match a corresponding first and second resonant frequency, by adjusting at least one of relative lengths of the FAS and SAS, a capacitance of the FAS, a location of the SAS relative to the FAS and a cross-sectional area of conducting elements forming the components of the antenna. The FAS is formed as an inverted E-shaped antenna having three branches. The first branch of the antenna is capacitive, a second branch provides a radio frequency signal feed and a third branch provides a shunt to ground. The SAS is formed as a mono-pole antenna that is formed integral with, and extends from, the FAS.

7 Claims, 8 Drawing Sheets

SYSTEMS AND METHODS FOR A DUAL BAND ANTENNA FOR AN INTERNAL MEDICAL DEVICE

BACKGROUND

Embodiments of the present embodiments described herein generally relate to implantable medical devices, and more particularly to antennas for use therein.

An implantable medical device ("IMD") is a medical device that is configured to be implanted within a patient anatomy and commonly employ one or more leads with electrodes that either receive or deliver voltage, current or other electromagnetic pulses (generally "energy") from or to an organ or tissue for diagnostic or therapeutic purposes. In general, IMDs include a battery, electronic circuitry, such as a pulse generator and/or a processor module, that are hermetically sealed within a metal housing (generally referred to as the "can"), and a microprocessor that is configured to handle radio frequency (RF) communication with an external device, as well as control patient therapy.

IMDs are programmed and monitored by an external programmer or external home-based patient care system. RF circuitry and an antenna are embedded within the housing of the IMD, such as the header or adjacent to the header, to allow data communication with the external device or base system. In general, the IMD communicates bi-directionally with the external programmer or base system using the Medical Implant Communication Service ("MICS") specification. The MICS specification is defined under 47 C.F.R. 95.601-95.673 Subpart E (incorporated herein by reference) and ETSI EN 301 839-1 (incorporated herein by reference). The MICS protocol uses a frequency band between 402-405 MHz and a transmit power of approximately 25 microwatts.

To conserve batter power, the IMD may enter into a sleep mode after a predetermined period of idle communication. While in the sleep mode, the IMD may disable the RF circuitry that conducts the bi-directional communication, such as a MICS transceiver. The IMD may exit the sleep mode once a wake-up signal from an external device is detected. The wake-up signal is generally an on-off key modulation scheme (OOK) at a high frequency such as 2.4 GHz. The detection of the OOK modulation allows the IMD to detect high power signals without the need for a local oscillator and synthesizer in the receiver.

Problems have arisen in designing the antenna for use in the IMDs. In particular, there can be a loss of RF communication performance due to the reduction in size of the header and the housing (also called the "can" or "case") of the IMD. Further, attenuation is inherent to the system since the RF signal travels through the lossy human body. Another problem is that two antennas are used and tuned to two operating frequencies (near 400 MHz for bi-directional communication and 2.4 GHz for the wake-up signal), yet the size of the two antennas is limited by the size of the header (at least for devices where the antenna is to be fitted inside the header). Ideally, the antennas should each have a length equal to a quarter of the wave length of the operating frequency (near 400 MHz for bi-directionally communication and 2.4 GHz for the wake-up signal). However, due to the operating frequencies of the MICS protocol it is difficult to design two antennas that both fit within a device header while achieving the length of the operating frequencies needed for the IMD. Hence, for antennas to be housed in the device header, the antennas may be smaller than the quarter wavelength constraint resulting in antenna much smaller than needed for select performance.

Previously, it has been proposed to provide a loop or an inverted E-shaped configuration antenna 102 mounted on the IMD 10. For example, the inverted E-shaped antenna 102 shown in FIG. 1 and described in application titled "INVERTED E ANTENNA WITH CAPACITANCE LOADING FOR USE WITH AN IMPLANTABLE MEDICAL DEVICE", which is expressly incorporated herein by reference in its entirety. However, such antenna configurations may only be optimized for a single frequency (for example, 400 MHz) degrading the performance or range of operation of the IMD at the alternate operating frequency (for example, 2.4 GHz).

Alternatively, IMDs have been proposed that employ the use of two antennas. FIG. 2 illustrates a conventional inverted E-shaped antenna 122 and a mono-pole antenna 124, having a shorter antenna length optimized for higher frequencies, mounted on an IMD 20. However, the use of two antennas on IMDs is problematic due to space constraints in the header of the IMD and increased manufacturing costs.

Accordingly, there is a need to provide a dual band antenna, particularly for IMD applications, that addresses these and other issues. It is to this end that aspects of the embodiments described herein are generally directed.

SUMMARY

In accordance with embodiments herein, an implantable medical device (IMD) for implant within a patient is provided, comprising, a case, radio frequency (RF) communication components housed within the case, and a dual band antenna coupled to the RF communication components. The dual band antenna includes a first and second antenna sub-structure tuned to different first and second resonant frequencies, respectively.

Optionally, the first antenna sub-structure is formed as an inverted E-shaped antenna having three branches. A first branch of the antenna is capacitive, a second branch provides an RF signal feed and a third branch provides a shunt to ground. Additionally or alternatively, the second antenna sub-structure is formed as a mono-pole antenna that is formed integral with, and extends from, one of the first, second, and third branches of the inverted E-shaped antenna.

In accordance with embodiments herein, a method of providing a dual band antenna for use in an implantable medical device (IMD) for implant within a patient is provided. The IMD having a case and radio frequency (RF) communication components housed within the case. The method includes proving a dual band antenna and tuning the dual band antenna to different first and second resonant frequencies, respectively, wherein the dual band antenna exhibits a return loss of at least −10 dB at the first and second resonant frequencies. The method also includes configuring the dual band antenna to be coupled to the RF communication components in the case of the IMD. Additionally or alternatively, the dual band antenna may include a first and second substructure.

Optionally, the method includes tuning the dual band antenna by adjusting at least one of relative lengths of the first and second antenna sub-structures, a capacitance of the first antenna sub-structure, a location of the second antenna sub-structure relative to the first antenna sub-structure and a cross-sectional area of conducting elements forming the component of the antenna.

In accordance with embodiments herein, a dual band antenna mounted to a case of an implantable medical device (IMD) for implant within a patient is provided. The dual band antenna includes a first antenna sub-structure and a second antenna sub-structure. The first antenna sub-structure is formed as an inverted E-shaped antenna having three branches. The first branch of the antenna is capacitive, a second branch provides a radio frequency signal feed and a third branch provides a shunt to ground. The second antenna sub-structure is formed as a mono-pole antenna that is formed integral with, and extends from, the first antenna substructure. The first and second antenna sub-structures are separately tuned to match a corresponding first and second resonant frequency, respectively, by adjusting at least one of relative lengths of the first and second antenna sub-structures, a capacitance of the first antenna substructure, a location of the second antenna sub-structure relative to the first antenna sub-structure and a cross-sectional area of conducting elements forming the component of the antenna.

BRIEF DESCRIPTION OF THE DRAWINGS

These and other features, aspects, and advantages will be more fully understood when considered with respect to the following detailed description, the appended claims, and the accompanying drawings.

FIG. 8b illustrates a rearview of the dual band antenna illustrated in FIG. 8a.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
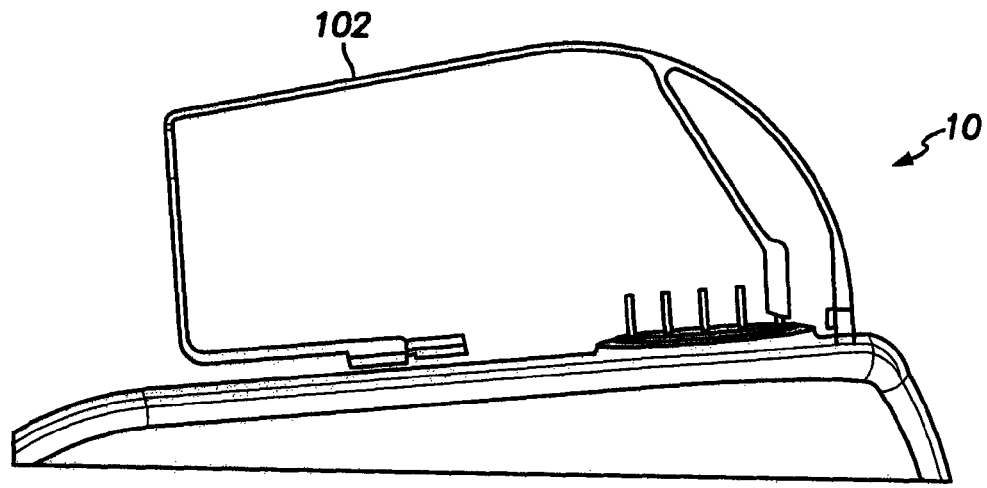
FIG. 1 illustrates a conventional inverted E-shaped antenna mounted within a header of an implantable medical device.
Figure 2:
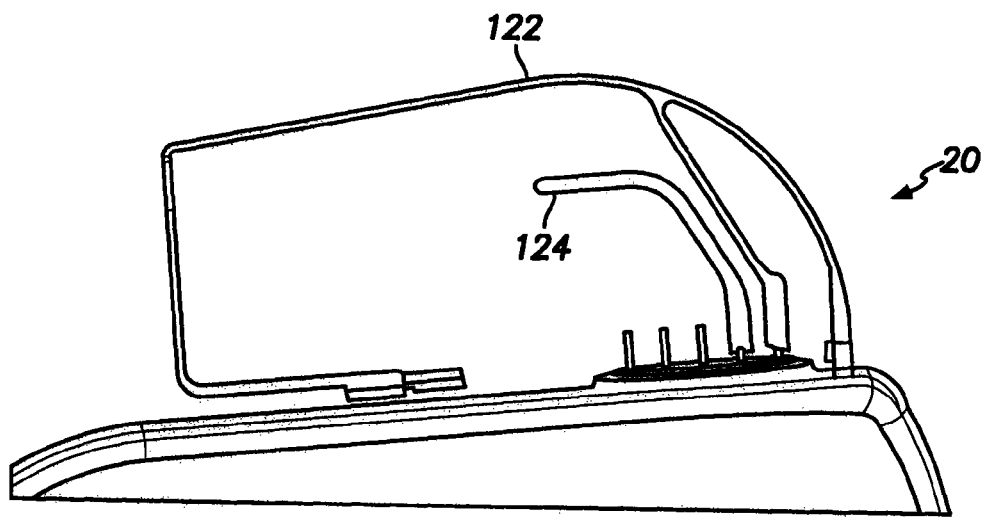
FIG. 2 illustrates a conventional inverted E-shaped antenna and a mono-pole antenna mounted within a header of the implantable medical device.
Figure 3:
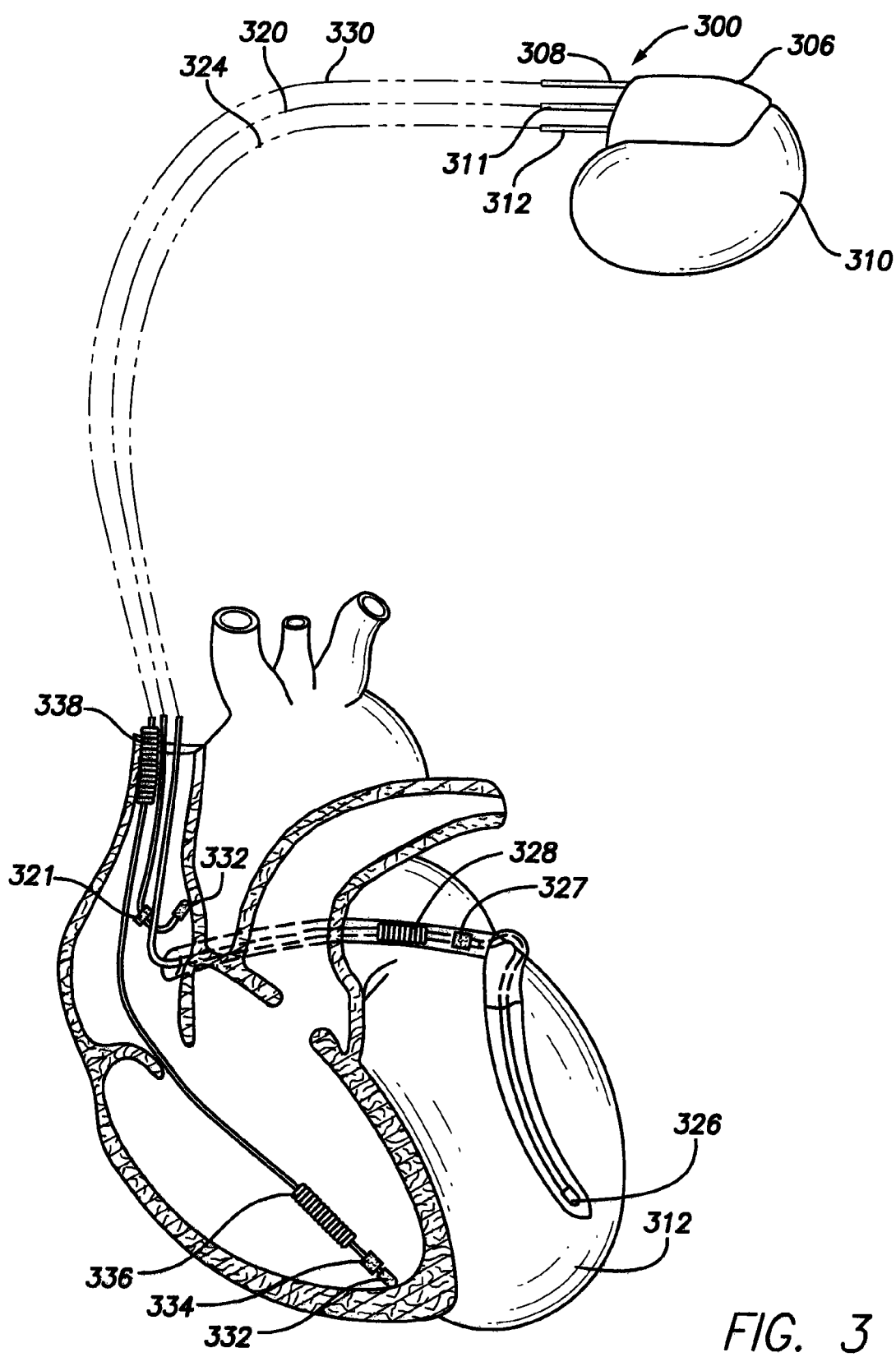
FIG. 3 illustrates pertinent components of an implantable medical system having an implantable medical device within a patient in accordance with various embodiments.

FIG. 3 illustrates an IMD 300 a heart 312 in a patient and implemented in accordance with one embodiment. The IMD 300 may be a cardiac pacemaker, an implantable cardioverter-defibrillator (ICD), a defibrillator, an ICD coupled with a pacemaker, and the like, implemented in accordance with one embodiment of the present invention. The IMD 300 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. The IMD 300 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. An exemplary structure for the IMD 300 is discussed and illustrated below in connection with FIG. 4.

The IMD 300 includes a housing 310 that is joined to a header assembly 306 that holds receptacle connectors 308, 311, 312 connected to a right ventricular lead 330, a right atrial lead 320, and a coronary sinus lead 324, respectively. The leads 330, 320, and 324 measure cardiac signals of the heart 312. The right atrial lead 320 includes an atrial tip electrode 322 and an atrial ring electrode 321. The coronary sinus lead 324 includes a left ventricular tip electrode 326, a left atrial ring electrode 327, and a left atrial coil electrode 328. The right ventricular lead 330 has an RV tip electrode 332, an RV ring electrode 334, an RV coil electrode 336, and an SVC coil electrode 338. The leads 330, 320, and 324 detect IEGM signals that form an electrical activity indicator of myocardial function over multiple cardiac cycles.

Figure 4:
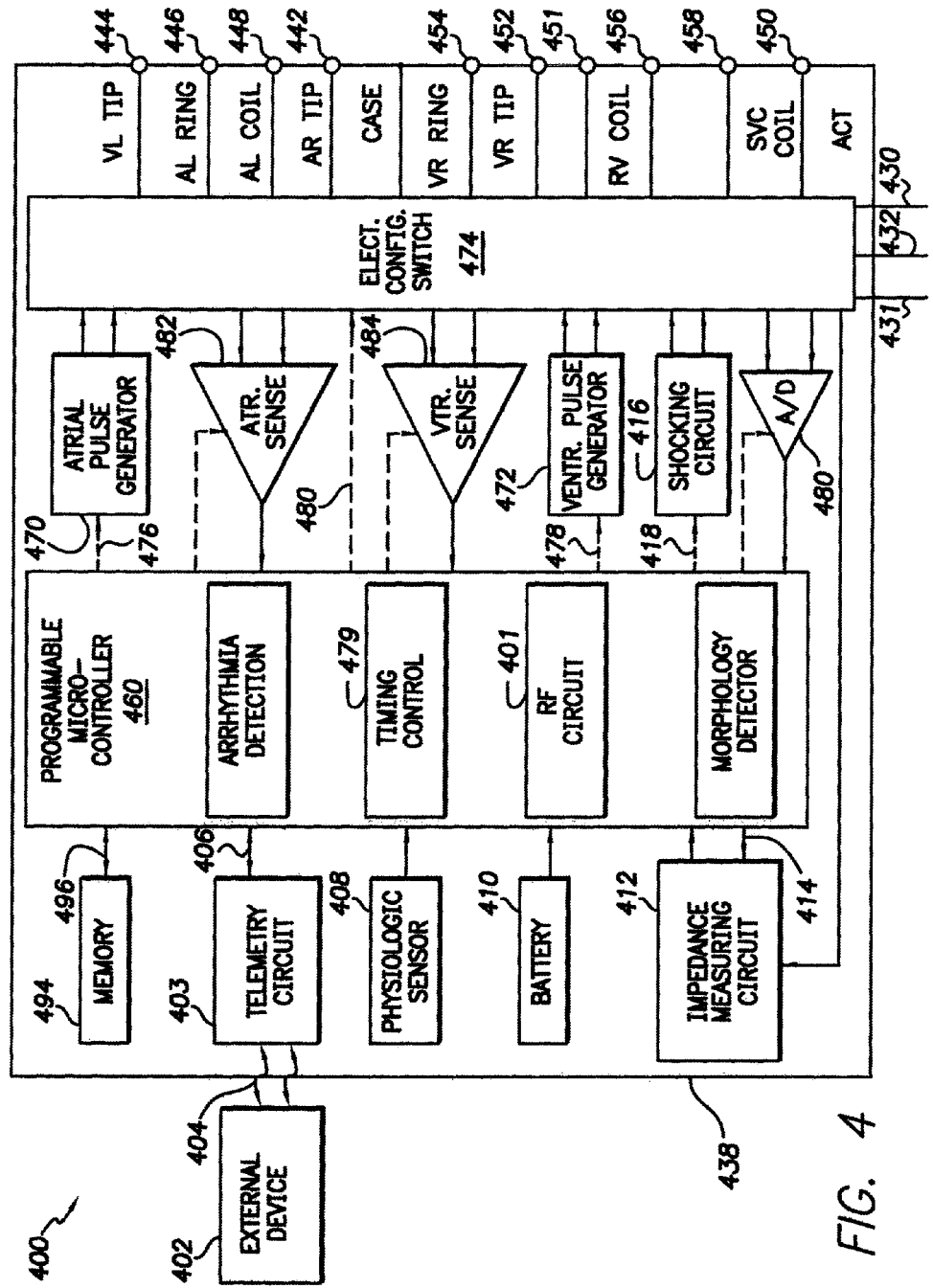
FIG. 4 illustrates a simplified block diagram of an implantable medical device in accordance with various embodiments.

FIG. 4 illustrates a block diagram of exemplary internal components of an IMD 400. The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

The IMD 400 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. A case 438 for IMD 400, shown schematically in FIG. 3, is often referred to as the "can", "housing" or "case electrode" and may be programmably selected to act as the return electrode for all "unipolar" modes. The casing 438 may further be used as a return electrode alone or in combination with one or more of the coil electrodes for shocking purposes. The casing 438 further may include a connector (not shown) having a plurality of terminals, 442, 446, 448, 452, 454, 456 and 458 (shown schematically and, for convenience, the names of the electrodes to which they are connected are shown next to the terminals). A right atrial tip terminal (AR TIP) 442 may be adapted for connection to the atrial tip electrode and a right atrial ring terminal may be adapted for connection to right atrial ring electrode. A left ventricular tip terminal (VL TIP) 444, a left atrial ring terminal (AL RING) 446, and a left atrial shocking terminal (AL COIL) 448 may be adapted for connection to the left ventricular ring electrode, and a left atrial tip electrode and a left atrial coil electrode respectively. A right ventricular tip terminal (VR TIP) 452, a right ventricular ring terminal (VR RING) 454, a right ventricular shocking terminal (RV COIL) 456, and an SVC shocking terminal (SVC COIL) 458 may be adapted for connection to the right ventricular tip electrode, right ventricular ring electrode, an RV coil electrode, and an SVC coil electrode, respectively.

An acoustic terminal (AC T) 450 may be adapted to be connected to an external acoustic sensor or an internal acoustic sensor, depending upon which (if any) acoustic sensors are used. Terminal 451 may be adapted to be connected to a blood sensor to collect measurements associated with glucose levels, natriuretic peptide levels, or catecholamine levels.

The IMD 400 may include a programmable microcontroller 460 which controls operation of the IMD 400. The microcontroller 460 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by program code stored in memory. The details of the design and operation of the microcontroller 460 are not critical to the invention. Rather, any suitable microcontroller 460 may be used that carries out the functions described herein. Among other things, the microcontroller 460 receives, processes, and manages storage of digitized cardiac data sets from the various sensors and electrodes. For example, the cardiac data sets may include IEGM data, pressure data, heart sound data, and the like.

The IMD 400 may include an atrial pulse generator 470 and a ventricular/impedance pulse generator 472 to generate pacing stimulation pulses for delivery by the right atrial lead 430, the right ventricular lead 431, and/or the coronary sinus lead 432 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The IMD 400 may include a neuro stimulation pulse generator circuit (not illustrated) to generate stimulation pulses for a brain or spinal cord nervous system. The stimulation pulses are delivered by a plurality of electrodes through a neuro output lead. The neuro stimulation pulse generator circuit may be controlled by the microcontroller 460 via appropriate control signals to trigger or generate the stimulation pulses.

The microcontroller 460 may further include timing control circuitry 479 used to control the timing of stimulation pulses (e.g., pacing rate, atria-ventricular (AV) delay, atrial interconduction (A-A) delay, or ventricular interconduction (V-V) delay, etc.), as well as, to keep track of the timing of refractory periods, blanking intervals, noise detection windows, evoked response windows, alert intervals, marker channel timing, and the like. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuit 482 and ventricular sensing circuit 484 may also be selectively coupled to the right atrial lead 430, coronary sinus lead 432, and the right ventricular lead 431, through the switch 474 for detecting the presence of cardiac activity in each of the four chambers of the heart. Accordingly, the atrial (ATR SENSE) and ventricular (VTR SENSE) sensing circuits, 482 and 484, may include dedicated sense amplifiers, multiplexed amplifiers or shared amplifiers. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

Cardiac signals are also applied to the inputs of an analog-to-digital (ND) data acquisition system 490. The data acquisition system 490 is configured to acquire IEGM signals, convert the raw analog data into a digital IEGM signal, and store the digital IEGM signals in memory 494 for later processing and/or radio frequency (RF) transmission to an external device 402. The data acquisition system 490 may be coupled to the right atrial lead 430, the coronary sinus lead 432, and the right ventricular lead 431 through the switch 474 to sample cardiac signals across any combination of desired electrodes. The data acquisition system 490 may also be coupled, through switch 474, to one or more of the acoustic sensors. The data acquisition system 490 acquires, performs ND conversion, produces and saves the digital pressure data, and/or acoustic data.

The microcontroller 460 may control the acoustic sensor and/or a physiologic sensor to collect heart sounds during one or more cardiac cycles. The heart sounds include sounds representative of a degree of blood flow turbulence. The acoustic sensor and/or physiologic sensor collects the heart sounds that include S1, S2 and linking segments. The S1 segment is associated with initial systole activity. The S2 segment is associated with initial diastole activity. The linking segment is associated with at least a portion of heart activity occurring between the S1 and S2 segments during a systolic interval between the initial systole and diastole activity. The microcontroller 460 changes a value for at least one of the pacing parameters between the cardiac cycles. The microcontroller 460 implements one or more processes described herein to determine values for one or more pacing parameters that yield a desired level of hemodynamic performance.

The microcontroller 460 is coupled to memory 494 by a suitable data/address bus 496, wherein the programmable operating parameters used by the microcontroller 460 are stored and modified, as required, in order to customize the operation of IMD 400 to suit the needs of a particular patient. The memory 494 also stores data sets (raw data, summary data, histograms, etc.), such as the IEGM data, heart sound data, pressure data, SvO2 data and the like for a desired period of time (e.g., 1 hour, 24 hours, 1 month). The memory 494 may store instructions to direct the microcontroller 460 to analyze the cardiac signals and heart sounds identify characteristics of interest and derive values for predetermined statistical parameters. The IEGM, pressure, and heart sound data stored in memory 494 may be selectively stored at certain time intervals, such as 5 minutes to 1 hour periodically or surrounding a particular type of arrhythmia of other irregularity in the heart cycle. For example, the memory 494 may store data for multiple non-consecutive 10 minute intervals.

The IMD 400 may also include an accelerometer or other physiologic sensor 408, commonly referred to as a "rate-responsive" sensor because it is typically used to record the activity level of the patient or adjust pacing stimulation rate according to the exercise state of the patient. Optionally, the physiological sensor 408 may further be used to detect changes in cardiac output, changes in the physiological condition of the heart, or changes in activity (e.g., detecting sleep and wake states) and movement positions of the patient. While shown as being included within IMD 400, it is to be understood that the physiologic sensor 408 may also be external to the IMD 400, yet still be implanted within or carried by the patient. A common type of rate responsive sensor is an activity sensor incorporating an accelerometer or a piezoelectric crystal, which is mounted within the casing 438 of the IMD 400.

The physiologic sensor 408 may be used as the acoustic sensor that is configured to detect the heart sounds. For example, the physiologic sensor 408 may be an accelerometer that is operated to detect acoustic waves produced by blood turbulence and vibration of the cardiac structures within the heart (e.g., valve movement, contraction and relaxation of chamber walls and the like). When the physiologic sensor 408 operates as the acoustic sensor, it may supplement or replace entirely acoustic sensors. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 400 includes a battery 410, which provides operating power to all of the circuits shown. The IMD 400 is shown as having impedance measuring circuit 412 which is enabled by the microcontroller 460 via a control signal 414. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 474 so that impedance at any desired electrode may be obtained.

The IMD 400 may also be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 460 may further control a shocking circuit 416 by way of a control signal 418. The shocking circuit 416 may generate shocking pulses of low (e.g., up to 0.5 joules), moderate (e.g., 0.5-10 joules), or high energy (e.g., Z11 to 40 joules), as controlled by the microcontroller 460. Such shocking pulses are applied to the patient's heart 312 through shocking electrodes. It is noted that the shock therapy circuitry is optional and may not be implemented in the IMD 400.

The pacing and other operating parameters of the IMD 400 may be non-invasively programmed into the memory 494 through a telemetry circuit 403 in telemetric communication 404 with the external device 402, such as a programmer, trans-telephonic transceiver, or a diagnostic system analyzer. The telemetry circuit 403 is activated by the microcontroller 460 by a control signal 406. The telemetry circuit 403 allows intra-cardiac electrograms, pressure data, acoustic data, SvO2 data, and status information relating to the operation of the IMD 400 (as contained in the microcontroller 460 or memory 494) to be sent to the external device 402 through an established communication link 404.

Depending upon the implementation, the microcontroller 460 may use an RF circuit 401. The RF circuit 401 includes RF communication components, such as a monolithic microwave integrated circuit (MMIC), coupled to a dual band antenna (not specifically shown in FIG. 4). The RF circuit 401 allows the IMD 400 to facilitate telemetry using a wireless communication protocol such as Bluetooth low energy, Bluetooth, WiFi, Medical Implant Communication Service ("MICS"), WiFi, or the like. Wireless protocol firmware is stored in memory 494, and is accessed by the microcontroller 460 via the data bus 496. The protocol firmware provides the wireless protocol syntax for the microcontroller 460 to assemble data packets, establish communication links, and partition data received from the external device 402 through the dual band antenna coupled to the RF circuit 401. The RF circuit 401 may support one or multiple wireless communication protocols that use varying operational frequencies.

Figure 5:
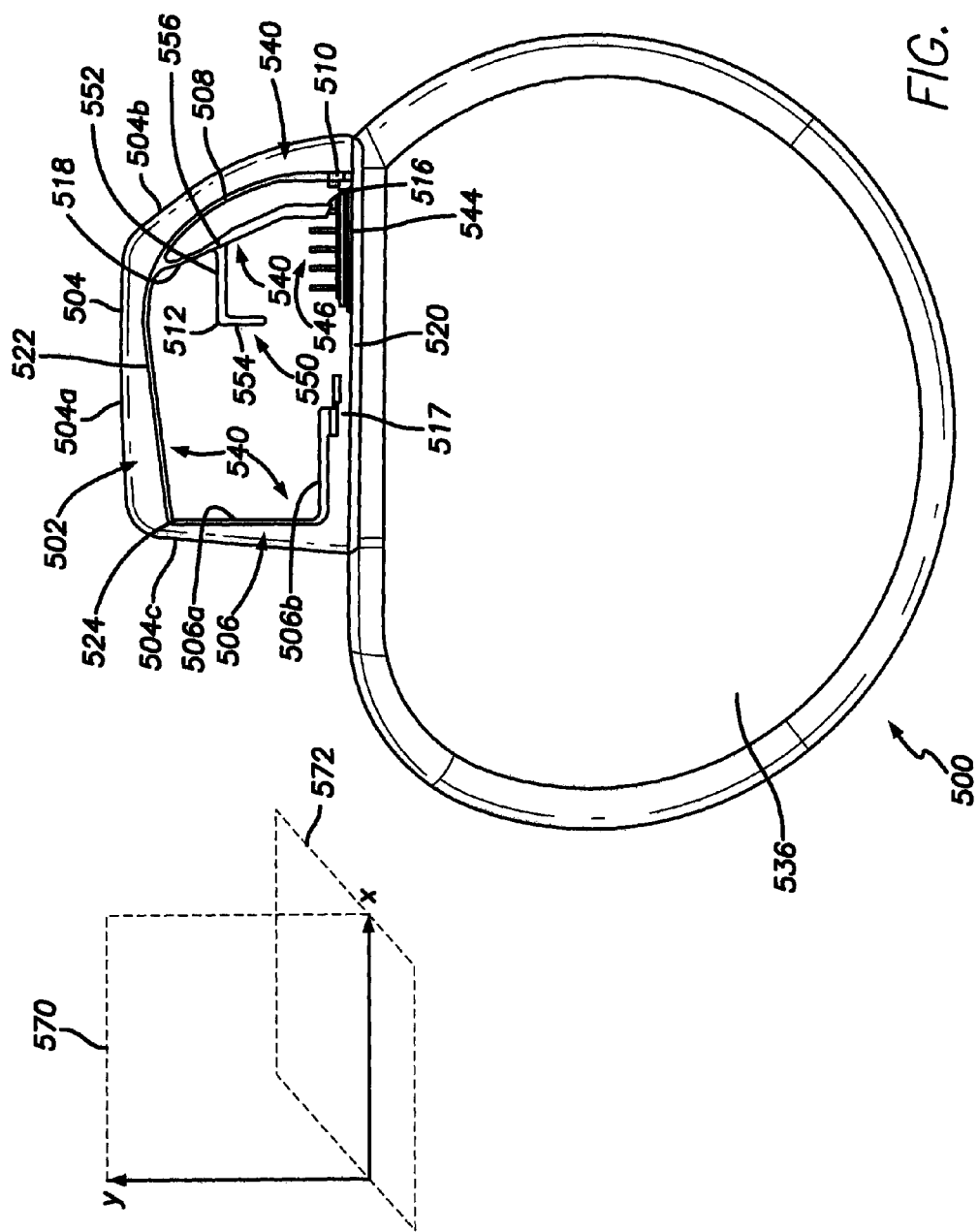
FIG. 5 illustrates an implantable medical system having a dual band antenna mounted within a header of the implantable medical device in accordance with various embodiments.

FIG. 5 illustrates an IMD 500 having a dual band antenna 502 installed within a header 504 mounted atop a case (or housing or can) 536 of the IMD 500. FIG. 5 illustrates the header 504 as transparent, however, the header 504 may be opaque in various other embodiments. The dual band antenna 502 may be, as illustrated, an omnidirectional antenna such that the dual band antenna 502 radiates or receives RF electromagnetic fields uniformly or equally in all horizontal directions or along a horizontal plane 572 perpendicular to a base plane 570 of the case 536. Thus, the dual band antenna 502 may transmit or receive wireless communications equally without limiting the position of the IMD 500 within the patient with respect to the external device (e.g., 402).

The dual band antenna 502 may include a first antenna sub-structure 540 and a second antenna sub-structure 550. The first antenna sub-structure 540 may have an inverted E-shaped antenna form factor within and extending along a common antenna plane aligned with the base plane 570 of the case 536. The first antenna sub-structure 540 may have three branches 506, 508, and 518 protruding from a main conducting arm 522 that provides a "backbone" for the dual band antenna 502. The three conducting branches 506, 508, and 518 extend from the main conducting arm 522 and connect to the case 536 and/or the internal components of the IMD 500.

A capacitive branch 506 is positioned at a backend of the header 504c, extending from a sharp bend 524 of the main conducting arm 522 and projecting towards the case 536 along the common antenna plane. The capacitive branch 506 includes a capacitor 517 mounted along a distal end of the capacitive branch 506, away from the sharp bend 524, which is in turn electrically coupled to a conducting surface 520. The conducting surface 520 or a top flat surface of the case 536 is aligned along the horizontal plane 572 and extends from a front end 504b to the back end 504c of the header providing a ground plane for the dual band antenna 502.

Additionally or alternatively, the capacitive branch 506 may have an L form factor with a leg segment 506a and a foot segment 506b with the capacitor 517 mounted at one end of the foot segment 506b. The leg segment 506a integrally joins to the main conducting arm 522 at the sharp bend 524 and extends towards the case 536 along the common antenna plane. The foot segment 506b may project from the distal end of the leg segment 506a, proximate to the case 536, towards the front end of the header 504b along the horizontal plane 572.

An RF signal feed branch 518 may be positioned between the capacitive branch 506 and an inductive branch 508 at a central portion of the header 504. The RF signal feed branch 518 extends from the main conducting arm 522 towards the case 536 along the common antenna plane. The RF signal feed branch 518 is coupled to the RF components (e.g., RF circuit 401) of the IMD 500 via an RF lead connection 516. The RF lead connection 516 is coupled to at least one of a set of feedthroughs 546 of a terminal 544 mounted to the case 536. It should be noted, the RF signal feed branch 518 may be mounted at a position closer to the frontend 504b or the backend 504c of the header traversing along the main conducting arm 522, as appropriate.

The inductive branch 508 is positioned at the frontend of the header 504b extending from the main conducting arm 522, having a smooth curve, towards the case 536. The inductive branch 508 is coupled at 510 to the conducting surface 520 to provide a shunt to ground. A length of the inductive branch 508 may be adjusted during antenna design to vary the inductance of the dual band antenna 502 to help achieve a desired impedance and/or resonant frequency of the dual band antenna 502. Additionally or alternatively, a discrete inductor may be mounted to the inductive branch 508 (or elsewhere on the dual band antenna 502) to provide additional impedance or to electrically lengthen the inverted E-shaped antenna to increase the resonant frequency, if desired.

The positions and lengths of the inductive and capacitive branches, 508 and 506, may depend upon the form factor of the header 504 and what is required for select performance (e.g., a signal return loss of −10 dB). Although not shown in FIG. 5 (see FIGS. 8a and 8b), additional components may be mounted within the header, such as components for connecting the IMD 500 to the proximal ends of pacing or sensing leads near the heart. The additional components may communicate to the internal components of the IMD (e.g., the electrode configuration switch 474) via the alternative feedthroughs 546 of the terminal 544.

The second antenna sub-structure 550 is formed as a mono-pole antenna 512 extending from the RF signal feed branch 518 at node 556 extending along the common antenna plane or the base plane 570 of the case 536. The mono-pole antenna 512 may include, as illustrated in FIG. 5, a leg segment 552 and a foot segment 554. The leg segment 552 is integrally joined to the RF signal feed branch 518 at node 556 and extends towards the backend of the header 504c parallel to the horizontal plane 572. The foot segment 554 may extend in a transverse direction from a distal end of the leg segment 506a, proximate to the backend 504c, projecting towards the case 536. Additionally, a position of the node 556 may be adjusted such that the distance changes between the second antenna sub-structure 550 in relation to the conducting surface 520 by traversing the node 556 along the RF signal feed branch 518.

Each antenna sub-structure 540 and 550 may be tuned to predetermined resonant frequencies such that each antenna sub-structure 540 and 550 provides a signal performance exhibiting a lower return loss at the predetermined resonant frequency relative to alternative frequencies. The resonant frequency of each antenna sub-structure 540 and 550 may be tuned by adjusting, for example the relative dimensions of the antenna sub-structure 540 and 550 (e.g., adjusting the length of the capacitive branch 506 and/or inductive branch 508, adjusting the length of the mono-pole antenna 512); location of the second antenna sub-structure 550 relative to the first antenna sub-structure 540, type of material or metal used to construct the antenna sub-structures 540 and 550 and/or the branches 506, 508, and 518, the cross sectional thickness, area, or shape of the antenna sub-structures 540 and 550 and/or the branches 506, 508, and 518, or the like. Optionally, each antenna sub-structure 540 and 550 may have a purely resistive feed-point impedance (e.g., not reactive or imaginary component) at the predetermined resonant frequencies.

Figure 6:
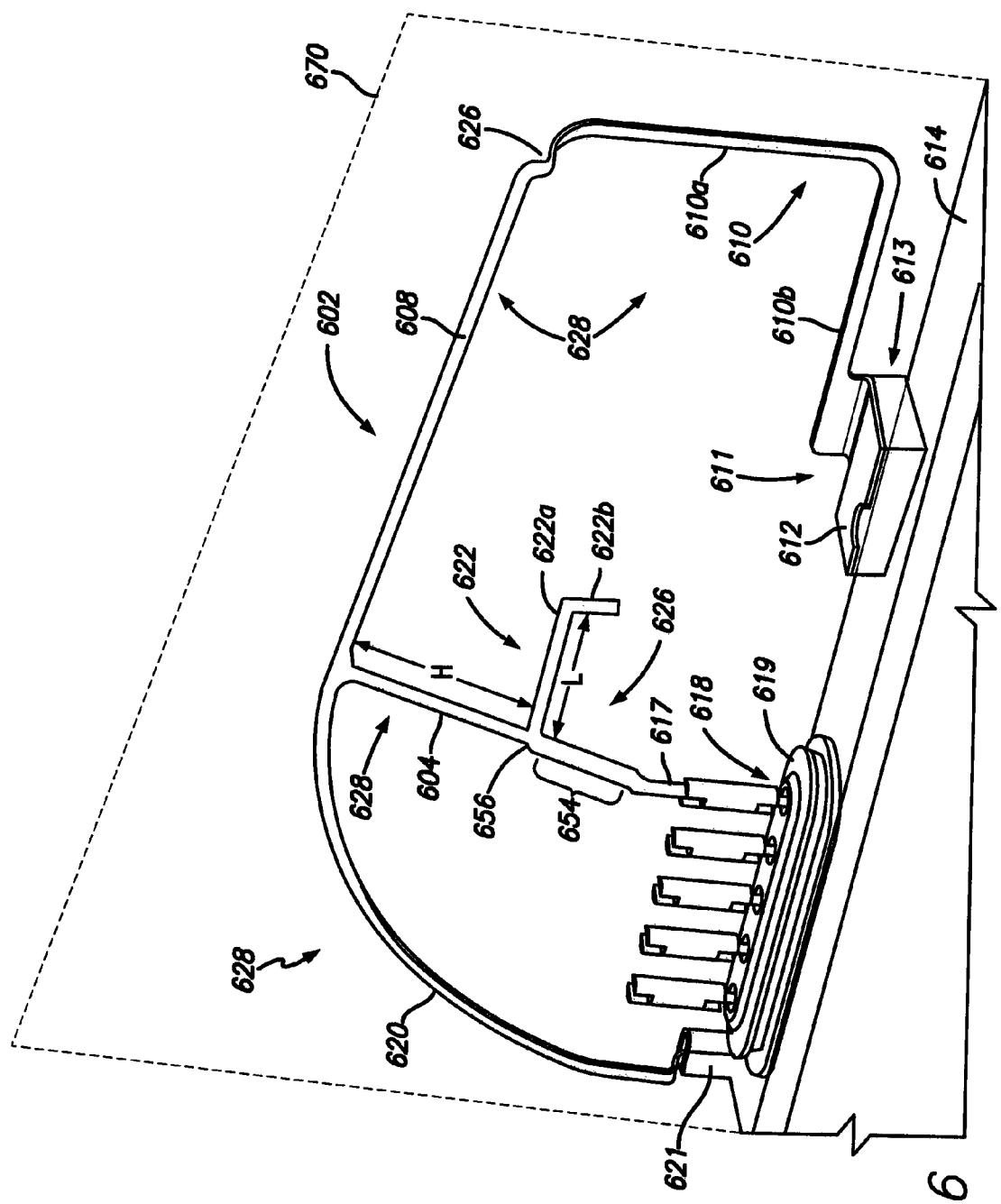
FIG. 6 illustrates a dual band antenna mounted within a header of the implantable medical device in accordance with various embodiments.
Figure 7:
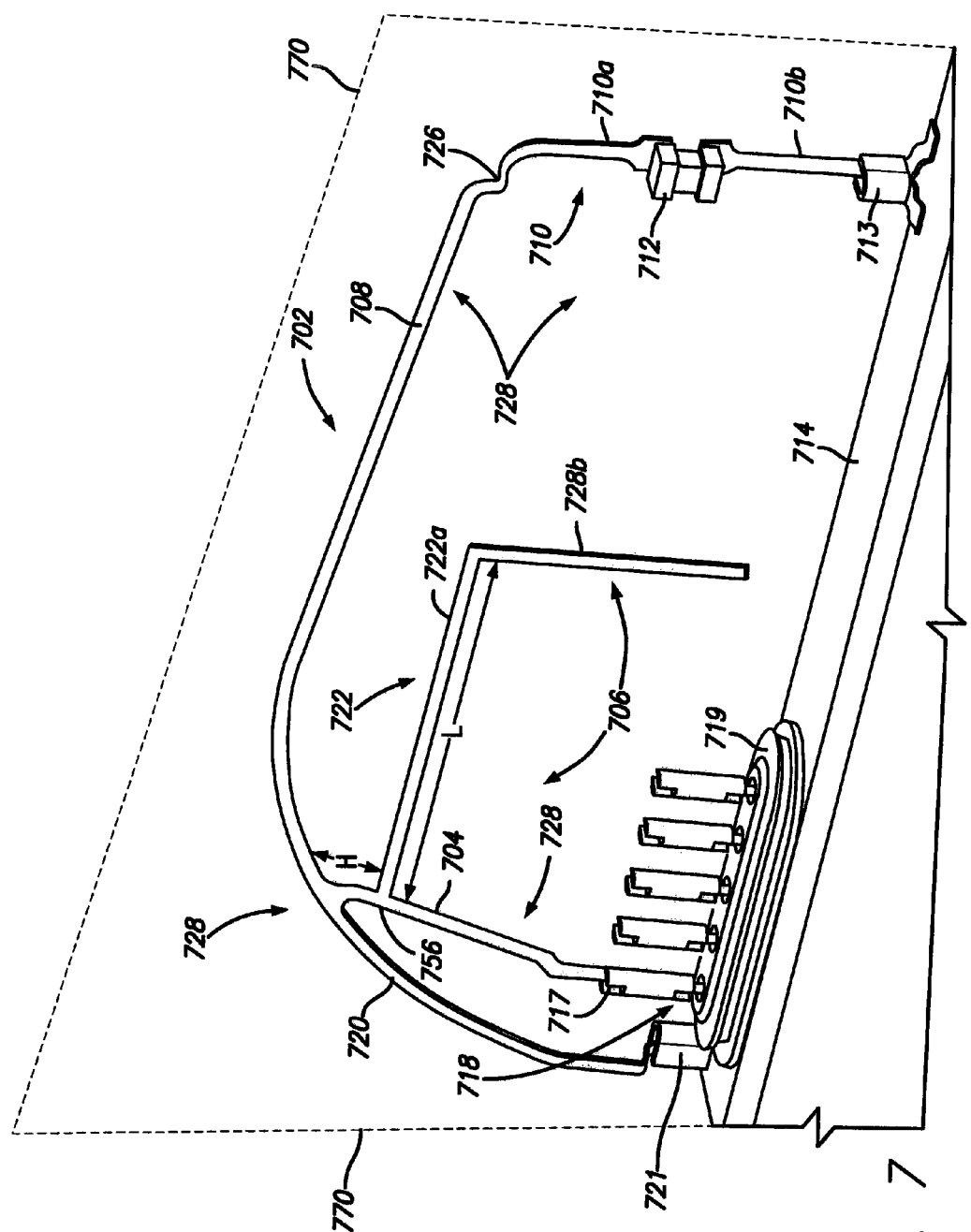
FIG. 7 illustrates a dual band antenna mounted within a header of the implantable medical device in accordance with various embodiments.

FIGS. 6-7 illustrate exemplary embodiments of dual band antennas, 602 and 702, mounted within headers (not shown) of separate IMDs. FIGS. 6-7 illustrate exemplary dual band antennas 602 and 702 including first and second antenna sub-structures 606, 628, 706, and 728. The first antenna sub-structures 628 and 728 have an inverted E-shaped form factor within and extending along common antenna planes 670 and 770 parallel with a base plane of the respective cases. The first antenna sub-structures 628 and 728 include main conducting arms 608 and 708 each having conducting branches, such as, capacitive branches 610 and 710, inductive branches 620 and 720, and RF signal feed branches 604 and 704.

The capacitive branch 610 of FIG. 6 has an L form factor with a leg segment 610a and a foot segment 610b. The leg segment 610a is integrally joined to the main conducting arm 608 at a sharp bend 626 of the main conducting arm 608 and extends towards a conducting surface 614. The foot segment 610b projects from the distal end of the leg segment 610a, proximate to the conducting surface 614, towards the inductive branch 620 parallel to a horizontal plane that is perpendicular to the common antenna plane 670. The foot segment 610b includes, at the distal end, proximate to the inductive branch 620, an integrated parallel plate capacitor 611. The integrated parallel plate capacitor 611 includes a generally flat or plate-shaped portion 612. The plate capacitor 611 is mounted via a dielectric epoxy 613 (or another suitable plastic material) to a conducting surface 614 to provide capacitance. The plate portion 612 is oriented to extend generally aligned in parallel with the horizontal plane (e.g. plane 572). The capacitance of the integrated parallel plate capacitor 611 may be altered by adjusting a position (e.g., spacing between, orientation relative to, lateral shift between centers thereof) of the plate portion 612 relative to the conducting surface 614 and/or an area or dimensions of the plate portion 612. For example, the capacitance may be increased by reducing the distance between the conducting surface 614 and the plate portion 612. It should be noted that since the integrated parallel plate capacitor 611 is not isolated, the presence of metal components such as a monopole antenna 622 of the second antenna sub-structure 606 may affect the impedance (e.g., increase the impedance due to the increased capacitance) and resonance frequencies of the first antenna sub-structure 628.

The capacitive branch 710 of FIG. 7 is integrally joined to the main conducting arm 708 at a sharp bend 726 of the main conducting arm 708 and extends towards a conducting surface 714. The capacitive branch 710 includes, a discrete surface mount capacitor 712 mounted in series between an upper portion of the capacitive branch 710*a* and a lower portion of the capacitive branch 710*b*. The lower portion of the capacitive branch 710*b* is coupled to an RF case connector 713, which is mounted to a conducting surface 714 inside the header (not shown). Unlike the integrated parallel plate capacitor 611, the discrete surface mount capacitor 712 is packaged or insulated from the effects of proximate metal components, such as from a mono-pole antenna 722, to the capacitive branch 710 impacting the impedance and resonant frequency of the dual band antenna 702.

The inductive branches 620 and 720 extend from a distal end of the main conducting arms 608 and 708, away from the sharp bends 626 and 726, towards the conducting surfaces 614 and 714. The inductive branches 620 and 720 are coupled to the conducting surfaces 614 and 714 via RF case connectors or terminals 621 and 721 to provide a shunt to ground.

The RF signal feed branches 604 and 704 are positioned between the capacitive branches 610 and 710 and the inductive branches 620 and 720. The RF signal feed branches 604 and 704 are connected to internal RF components of the IMD (e.g., the IMD 500) via RF lead connections 617 and 717 each coupled to at least one of a set of feedthroughs 618 and 718 of terminals 619 and 719 mounted to the cases of the respective IMDs. The feedthroughs 618 and 718 may include an outer conductor that is grounded to the case or housing, an inner conductor which is a pin running through the center of the feedthrough, and/or a dielectric material that separates the inner and outer conductor. Inside the case, the feedthrough pins may be connected to the RF circuitry and transceiver (e.g., RF circuit 401).

The second antenna sub-structures 606 and 706 are formed as mono-pole antennas 622 and 722 of differing lengths extending from the RF signal feed branches 604 and 704 at nodes 656 and 756 towards the capacitive branches 610 and 710. Optionally, the mono-pole antennas may extend from the RF signal feed branches 604 and 704 towards the inductive branches 620 and 720.

The mono-pole antenna 622 includes two arm segments 622*a* and 622*b* (e.g., leg and foot segment) having a folded monopole or L shaped form factor. Optionally, the mono-pole antenna 622 may have only one arm segment. The first arm segment 622*a* is integrally joined to the RF signal feed branch 604 and extends from the RF signal feed branch 604 at node 656, positioned a distance H from the main conducting arm 608, along the horizontal plane parallel to the conducting surface 614 towards the capacitive branch 610. At a distal end of the first arm segment 622*a*, proximate to the capacitive branch 610, the second arm segment 622*b* extends in a traverse direction from the distal end of the first arm segment 622*a* towards the conductive surface 614.

A length of the mono-pole antenna 622 represents a distance current travels from the distal end of the arm segment 622*b*, proximate to the conducting surface 614, through the node 656 to the RF lead connection 617. The length of the mono-pole antenna includes the sum of the lengths of the two arm segments 622*a* and 622*b*, and is based on a position of the mono-pole antenna 622 relative to the conducting surface 614 and/or main conducting arm 608. The length of the mono-pole antenna 622 may be adjusted to tune the second antenna sub-structure 606 to the predetermined resonant frequency (e.g., 2.4 GHz) by having the length of the mono-pole antenna 622 approximately a fraction of the wavelength (e.g., ½, ¼, ⅛) of the predetermined resonant frequency.

For example, the two arm segments 622*a* and 622*b* have a length of 0.5 inches and 0.25 inches respectively, and the mono-pole antenna 622 is positioned 0.5 inches from the RL lead connection 617 such that the length of the second antenna sub-structure 606 is 1.25 inches. The predetermined resonant frequency is 1 GHz thus having a wavelength of approximately 11.8 inches. The length of the second antenna sub-structure 606, to be tuned to the predetermined resonant frequency, may be adjusted to ⅛ of the wavelength or approximately 1.47 inches. The second antenna sub-structure 606 may be tuned by extending the length of both or either of the two arm segments 622*a* and 622*b* of the mono-pole antenna 622 by 0.22 inches. Additionally or alternatively, the position of the node 656 may be raised such that the distance H is decreased, thus increasing the distance between the mono-pole antenna 622 and the RF lead connection 617.

In an additional example, the predetermined resonant frequency is 2.4 GHz thus having a wavelength of approximately 4.92 inches. The length of the second antenna sub-structure 606, to be tuned to the predetermined resonant frequency, may be adjusted to ⅛ of the wavelength or approximately 0.6 inches. The second antenna sub-structure 606 may be tuned by decreasing the length of at least one of the two arm segments 622*a* and 622*a* of the mono-pole antenna 622 and/or the position of the node 656 by increasing the distance H.

It should be noted, from the above examples that the lengthening or extending the length of the second antenna sub-structure 606 decreases the tuned predetermined resonant frequency of the second antenna sub-structure 606. Alternatively, decreasing or shortening the length of the second antenna sub-structure 606 increases the tuned predetermined resonant frequency of the second antenna sub-structure 606. Additionally or alternatively, the second antenna sub-structure 606 may be tuned by increasing or decreasing the impedance or inductance of the second antenna sub-structure 606 by adjusting a width or thickness of the mono-pole antenna 622 and/or a lower portion 654 of the RF signal feed branch 604.

The length of the mono-pole antenna 622, specifically the arm segments 622*a* and 622*b*, may be limited by the conductive surface 614 (affecting the length of the arm segment 622*b*) and/or obstruction by the capacitive branch 610 (affecting the length of the arm segment 622*a*). Similar to the mono-pole antenna 622, the mono-pole antenna 722 includes two arm segments 722*a* and 722*b* having a folded monopole or L shaped form factor. A position of the RF signal feed branch 704 is adjusted, relative to the RF signal feed branch 604, by traversing the RF signal feed branch 704 along the main conducting arm 708 closer to the inductance branch 720. The position of the RF signal feed branch 704 increases a distance between the RF signal feed branch 704 and the capacitive branch 710 relative to the position illustrated in FIG. 6. One result of the adjusted position of the RF signal feed branch 704 is the ability to have longer arm segments 722*a* and 722*b* and thus lower resonant frequencies than those possible for the arm segments 622*a* and 622b. As noted above, increasing the length of the second antenna sub-structure 706, such as by increasing the length of the arm segments 722a and 722b allow the second antenna sub-structure 706 to be tuned to lower predetermined resonant frequencies.

Figure 8A:
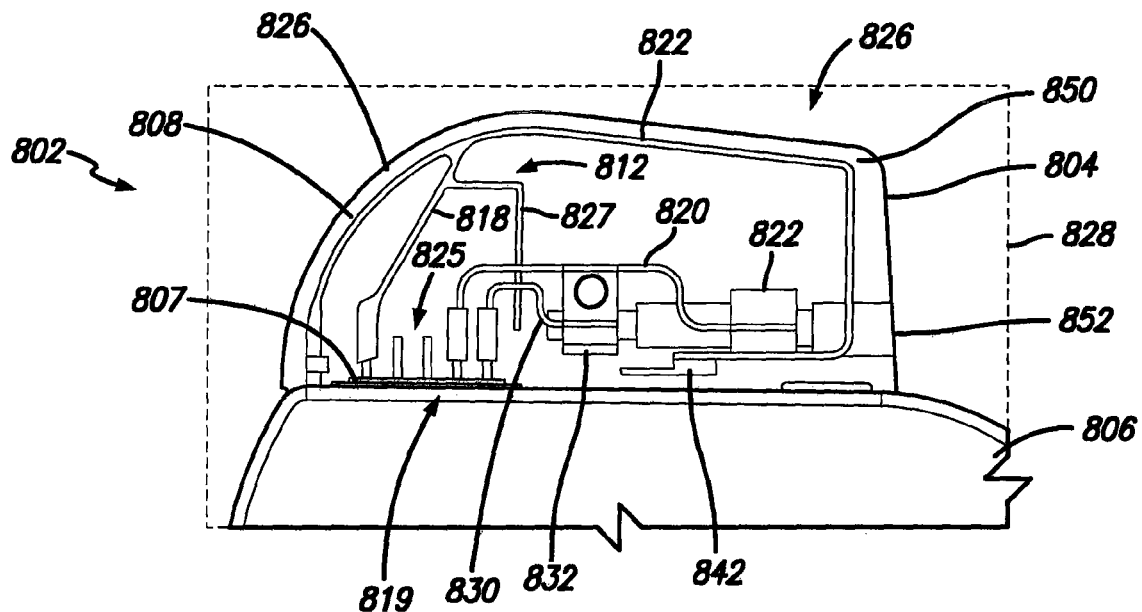
FIG. 8a illustrates a dual band antenna mounted within a header of the implantable medical device in accordance with various embodiments.

FIG. 8a illustrates one exemplary embodiment of a dual band antenna 802 mounted within a header 804 of a case 806 of an IMD again including a first and second antenna sub-structure 826 and 812 as described above. The first antenna sub-structure 826 having an inverted E-shaped form factor extending along a common antenna plane 828 having a main conducting arm 822 with three conducting branches, a capacitive branch 810, an inductive branch 808, and an RF signal feed branch 818. The second antenna sub-structure 812 includes a mono-pole antenna 827 extending from the RF signal feed branch 818.

Additionally, FIG. 8a illustrates components 822 and 832 for connecting proximal ends of leads (e.g., leads 330, 320, and 324), proximate to the IMD, to measure cardiac signals of the heart 312 located at the distal end of the leads. The components 822 and 832 communicate to the internal components of the IMD (e.g., the electrode configuration switch 474) via connection lines 820 and 830 coupled to lead connections 819. The lead connections 819 are coupled to a set of feedthroughs 825 of a terminal 807 mounted to the case 806. For example, component 832 may be a ring connector for connecting conductors within the leads that are coupled to ring electrodes (e.g., 321, 327, 334) at the distal ends of the leads, proximate to the heart 312. In addition, component 822 may be a tip connector for connecting to conductors of the leads that are coupled to tip electrodes (e.g., 322, 326, 332) at the distal ends of the leads, proximate to the heart 312.

Figure 8B:
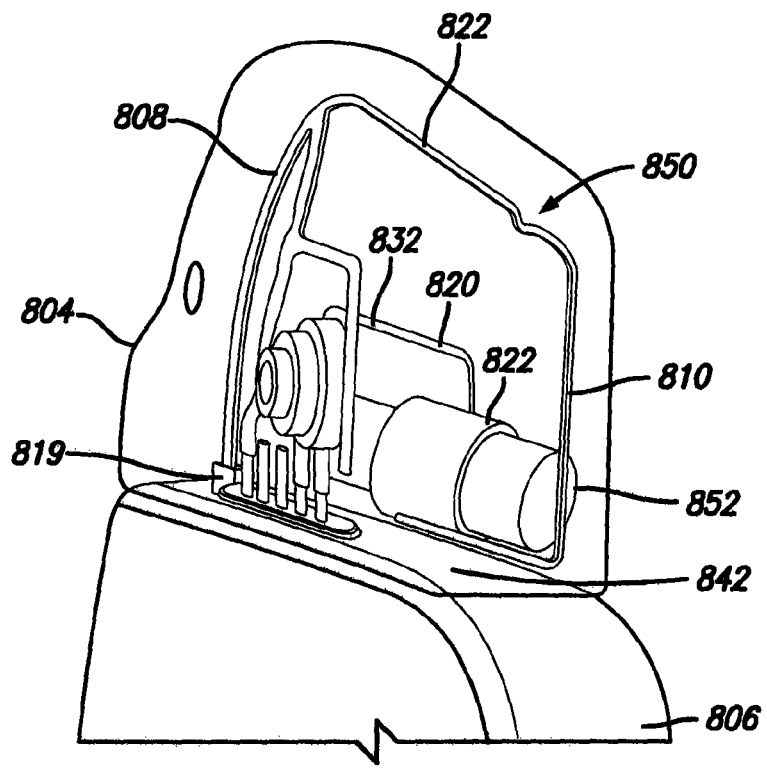

FIG. 8b illustrates a rearview of the exemplary embodiment of the dual band antenna 802 shown in FIG. 8a. The capacitive branch 810 is shown displaced having a different horizontal position relative to the case 806 than the remaining structures of the dual band antenna 802 (e.g., the second antenna sub-structure 812, the RF signal feed branch 818, the main conducting arm 822, the inductive branch 808). At the distal end of the capacitive branch 810, proximate to the case 806, is an integrated parallel plate capacitor 842. The parallel plate capacitor 842 protrudes from the capacitive branch 810 such that the parallel plate capacitor 842 is positioned at an original horizontal position similar to the remaining structure of the dual band antenna 802 (e.g., the mono-pole antenna 827, the RF signal feed branch 818, the main conducting arm 822, the inductive branch 808).

Displacing the capacitive branch 810 allows, for example, the component 832 to connect to the external conductors via a header opening 852 without being obstructed by the dual band antenna 802, specifically, the capacitive branch 810. The capacitive branch 810 may be displaced at the proximal end of the capacitive branch 810 proximate to the main conducting arm 822 via a sharp bend 850. The sharp bend 850 shifts the proximal end of the capacitive branch 810 along the horizontal plane by curving the capacitive branch 810.

Figure 9:
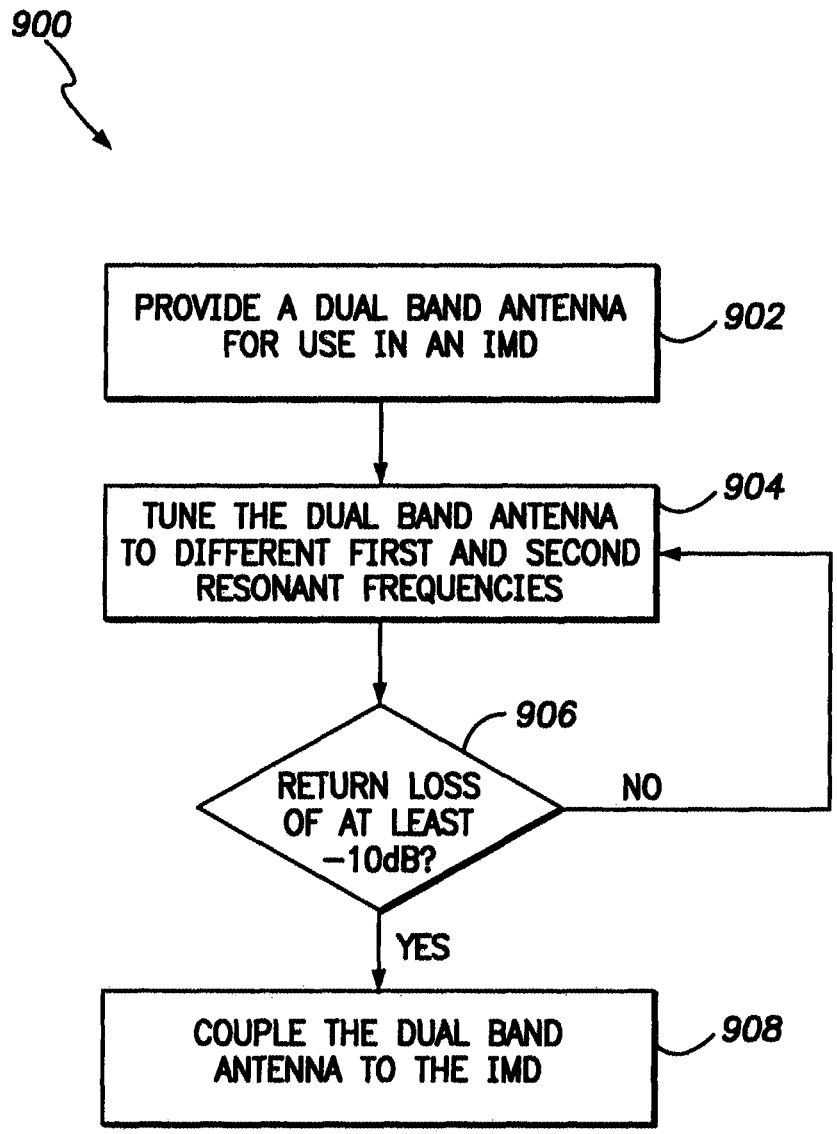
FIG. 9 illustrates a flow chart of a method to provide a dual band antenna for use in an implantable medical device for implant within a patient.

FIG. 9 illustrates a flowchart of a method 900 for providing a dual band antenna for use in an IMD for implant within a patient. The method 900 may be implemented as a software algorithm, package, or system that directs one or more hardware circuits or circuitry to perform the actions described herein. For example, the operations of the method 900 may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic thereof.

At least one technical effect of at least one portion of the method described herein includes i) providing a dual band antenna, ii) tuning the dual band antenna to different first and second resonant frequencies, respectively, having a return loss of at least −10 dB at the first and second resonant frequencies, and iii) configuring the dual band antenna to be coupled to the RF communication components in the case of the device.

Beginning at 902, provide a dual band antenna for use in an IMD. For example, the dual band antenna 502 described above having a first and second antenna sub-structures that may be tuned to two different resonant frequencies. Further, the dual band antenna 502 may be installed within the header 504 mounted to the case (or housing or can) 536 of the IMD 500 that provides a ground plane for the dual band antenna 502.

At 904, tune the dual band antenna to different first and second resonant frequencies such that, at 906, the dual band antenna exhibits a return loss of at least −10 dB at the first and second resonance frequencies. As described above, the first and second antenna sub-structures may be tuned to different resonant frequencies by adjusting either the lengths or electrical characteristics of the dual band antenna. The adjustments of the dual band antenna may continue until the return loss of at least −10 dB is measured.

For example, in an embodiment, the resonant frequency of the first antenna sub-structure may be adjusted by changing the capacitance of the capacitive branch 610 by changing the distance between the conducting surface 614 and the plate portion 612. Additionally or alternatively, the position of the mono-pole antenna 622 may be adjusted affecting (e.g., increasing or decreasing) the parasitic capacitance caused by the proximity of the mono-pole antenna 622 to the first antenna sub-structure 628. Optionally, the discrete surface mount capacitor 712 may be changed.

Alternatively or additionally, in an embodiment the resonant frequency of the first antenna sub-structure may be adjusted by changing the length of the inductive branch thus altering the inductance of the dual band antenna 502. Optionally, a discrete inductor may be mounted to the inductive branch 508 or elsewhere on the dual band antenna 502 to provide additional inductance or to electrically lengthen the inverted E-shaped antenna to tune the resonant frequency of the first antenna sub-structure.

For example, in an embodiment, the resonant frequency of the second antenna sub-structure may be adjusted by changing the length of the mono-pole antennas 622 and 722 by adjusting the length of the arm segments (e.g., 622a, 622b, 722a, 722b) or traversing the mono-pole antennas 622 and 722 along the RF signal feed branch 604 and 704 by changing the position of the nodes 656 and 756.

At 908, couple the dual band antenna to the IMD. As described above, the dual band antenna 502 may be mounted within the header 504 of the IMD 500. The RF signal feed branch 518 may be coupled to the RF components (e.g., RF circuit 401) of the IMD 500 via the RF lead connection 516 coupled to at least one of the set of feedthroughs 546 of the terminal 544 mounted on the case 536.

It should be understood that any "optimal" antenna parameters or dimensions described herein are not necessarily absolutely optimal in a mathematical sense. What constitutes "optimal" depends on the criteria used for judging the resulting performance. The antenna parameters identified or selected using techniques described herein represent, at least, a "preferred" set of parameters. Designers may choose to adjust or alter the parameters at their discretion during device design.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. An implantable medical device for implant within a patient, the device comprising:
   a case;
   radio frequency (RF) communication components housed with the case;
   a header mounted to the case, the header having a first end, a second end, a top portion and a bottom portion, with the bottom portion mounted to the case;
   a dual band antenna positioned within the header and coupled to the RF communication components, the dual band antenna including a first antenna sub-structure and a second antenna sub-structure, the dual band antenna further including an main conducting arm having a first end and a second end with the main conducting arm positioned in the top portion of the header between the first and second ends of the header;
   the first antenna sub-structure including an inductive branch having a first end and an second end, with the first end of the inductive branch connected to the second end of the main conducting arm, and the second end of the inductive branch shunted to ground;
   the first antenna sub-structure further including an L-shaped capacitive branch with the top of the L-shaped capacitive branch connected to and extending from the first end of the main conducting arm towards the case, with a capacitor mounted to end of the L-shaped capacitive branch distal to the top of capacitive branch;
   the first antenna sub-structure further including an RF signal feed branch positioned between the capacitive branch and the inductive branch, the RF signal branch having a first end connected to the second end of the main conduction arm and a second end being coupled to the RF communication components; and
   the second antenna sub-structure including a mon-pole antenna extending from the RF signal feed branch and connected to the RF signal feed branch intermediate the first and second ends of the RF signal branch.

2. The device of claim 1, wherein in the dual band antenna is generally planar.

3. The device of claim 1, wherein the second antenna sub-structure is L-shaped, with the top portion begin integrally joined to the RF signal feed branch and extending towards second end of the case.

4. The device of claim 3, wherein the bottom portion of the L-shaped second antenna sub-structure extending in a direction towards the case.

5. An implantable medical device for implant within a patient, the device comprising:
- a case;
- radio frequency (RF) communication components housed with the case;
- a header mounted to the case, the header having a first end, a second end, a top portion and a bottom portion, with the bottom portion mounted to the case;
- a planar dual band antenna positioned within the header and coupled to the RF communication components, the dual band antenna including a first antenna sub-structure and a second antenna sub-structure, the dual band antenna further including an main conducting arm having a first end and a second end with the main conducting arm positioned in the top portion of the header between the first and second ends of the header;
- the first antenna sub-structure including an inductive branch having a first end and an second end, with the first end of the inductive branch connected to the second end of the main conducting arm, and the second end of the inductive branch shunted to ground;
- the first antenna sub-structure further including an L-shaped capacitive branch with the top of the L-shaped capacitive branch connected to and extending from the first end of the main conducting arm towards the case, with a capacitor mounted to end of the L-shaped capacitive branch distal to the top of capacitive branch;
- the first antenna sub-structure further including an RF signal feed branch positioned between the capacitive branch and the inductive branch, the RF signal branch having a first end connected to the second and of the main conduction arm and a second end being coupled to the RF communication components; and
- the second antenna sub-structure including a mon-pole antenna extending from the RF signal feed branch and connected to the RF signal feed branch intermediate the first and second ends of the RF signal branch.

6. The device of claim 5, wherein the second antenna sub-structure is L-shaped, with the top portion begin integrally joined to the RF signal feed branch and extending towards second end of the case.

7. The device of claim 6, wherein the bottom portion of the L-shaped second antenna sub-structure extending in a direction towards the case.

* * * * *